US00PP16385P2

(12) United States Plant Patent
Hanes

(10) Patent No.: US PP16,385 P2
(45) Date of Patent: Mar. 28, 2006

(54) ***GERANIUM* PLANT NAMED 'CLIPS REDTHREE'**

(50) Latin Name: *Pelargonium×hortorum*
Varietal Denomination: Clips Redthree

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 157 days.

(21) Appl. No.: 10/818,341

(22) Filed: Apr. 5, 2004

(51) Int. Cl.
*A01H 5/00* (2006.01)

(52) U.S. Cl. ..... Plt./330
(58) Field of Classification Search ..... Plt./330
See application file for complete search history.

(56) References Cited

U.S. PATENT DOCUMENTS

PP13,004 P2 * 9/2002 Hanes ..... Plt./330

OTHER PUBLICATIONS

UPOV ROM GTITM Computer Database; GTI Jouve Retrieval Software 2004/06; citation for 'Clips Redthree'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Geranium* plant named 'Clips Redthree', characterized by its upright, outwardly spreading and rounded growth habit; freely basal branching habit; dark green-colored leaves; freely flowering habit with many flower umbels per plant; and flower umbels with numerous intense red-colored semi-double flowers.

1 Drawing Sheet

Botanical designation: *Pelargonium×hortorum.*
Variety denomination: 'Clips Redthree'.

BACKGROUND OF THE INVENTION

The present invention relates to a new and distinct cultivar of *Geranium* plant, botanically known as *Pelargonium×hortorum*, commercially known as a Zonal *Geranium*, and hereinafter referred to by the name 'Clips Redthree'.

The new *Geranium* is a product of a planned breeding program conducted by the Inventor in Gilroy, Calif. The objective of the breeding program is to develop new Zonal *Geranium* cultivars with good basal branching, freely flowering habit and attractive flower and foliage coloration.

The new *Geranium* originated from a cross-pollination made by the Inventor in January, 2000 of a proprietary *Pelargonium×hortorum* selection identified as code number 8326-1, not patented, as the female, or seed, parent with a proprietary *Pelargonium×hortorum* selection identified as code number 8344-2, not patented, as the male, or pollen, parent. The cultivar Clips Redthree was discovered and selected by the Inventor as a single flowering plant within the progeny from this cross-pollination in a controlled environment in Gilroy, Calif. in June, 2000.

Asexual reproduction of the new cultivar by terminal cuttings taken at Gilroy, Calif., since September, 2000 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Clips Redthree'. These characteristics in combination distinguish 'Clips Redthree' as a new and distinct *Geranium* cultivar:

1. Upright, outwardly spreading and rounded growth habit.
2. Freely basal branching habit.
3. Dark green-colored leaves.
4. Freely flowering habit with many large flower umbels per plant.
5. Flower umbels with numerous intense red-colored semi-double flowers.

In side-by-side comparisons conducted in Gilroy, Calif., plants of the new *Geranium* differed from plants of the female parent selection in the following characteristics:

1. Plants of the new *Geranium* had darker green-colored leaves than plants of the female parent selection.
2. Plants of the new *Geranium* and the female parent selection differed in flower color as plants of the female parent selection did not have as intense red-colored flowers.

In side-by-side comparisons conducted in Gilroy, Calif., plants of the new *Geranium* differed from plants of the male parent selection in the following characteristics:

1. Plants of the new *Geranium* were more vigorous than plants of the male parent selection.
2. Plants of the new *Geranium* and the male parent selection differed in flower color as plants of the male parent selection had scarlet-colored flowers.

The new *Geranium* can be compared to the cultivar, Clips Red II, disclosed in U.S. Plant Pat. No. 13,004. However, in side-by-side comparisons conducted in Gilroy, Calif., plants of the new *Geranium* differed from plants of the cultivar Clips Red II in the following characteristics:

1. Plants of the new *Geranium* were larger and more vigorous than plants of the cultivar Clips Red II.
2. Leaves of plants of the new *Geranium* were lighter green in color than leaves of plants of the cultivar Clips Red II; in addition, plants of the new *Geranium* did not have a distinct leaf zonation pattern whereas plants of the cultivar Clips Red II had a distinct zonation pattern.

3. Plants of the new *Geranium* had larger flowers than plants of the cultivar Clips Red II.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Clips Redthree'.

The photograph at the bottom of the sheet is a close-up view of typical flower umbels of 'Clips Redthree'.

Flower and foliage colors in the photographs may differ slightly from the color values cited in the detailed botanical description which accurately describe the colors of the new *Geranium*.

DETAILED BOTANICAL DESCRIPTION

Plants of the cultivar Clips Redthree have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Plants used for the photographs and description were about six months from planting rooted cuttings. In the following description, color references are made to The Royal Horticultural Society Colour Chart, 1995 Edition, except where general terms of ordinary dictionary significance are used.

Botanical classification: *Pelargonium×hortorum* cultivar Clips Redthree.

Parentage:

*Female parent.*—Proprietary *Pelargonium×hortorum* selection identified as code number 8326-1, not patented.

*Male parent.*—Proprietary *Pelargonium×hortorum* selection identified as code number 8344-2, not patented.

Propagation:

*Type cutting.*—Terminal cuttings.

*Time to initiate roots.*—About 12 to 14 days at 24° C.

*Time to develop roots.*—About four weeks at 18 to 24° C.

*Root description.*—Fibrous, fine, white in color.

*Rooting habit.*—Freely branching.

Plant description:

*General appearance.*—Upright, outwardly spreading and rounded growth habit.

*Growth and branching habit.*—Vigorous and very freely basal branching with about 10 lateral branches. Pinching, that is, removal of terminal apices, is typically not required.

*Plant height to top of foliage.*—About 19 cm.

*Plant height to top of flower umbels.*—About 32 cm.

*Plant width.*—About 47 cm.

*Lateral branches.*—Length: About 23 cm. Diameter: About 1 cm. Internode length: About 2.3 cm. Texture: Pubescent. Color: 144A.

*Foliage description.*—Arrangement: Alternate, simple. Length: About 6 cm. Width: About 10 cm. Shape: Reniform with slight round lobing. Apex: Rounded. Base: Cordate. Margin: Crenate, ruffled to sinuate. Venation: Palmate. Texture, upper and lower surfaces: Velvety; pubescent; somewhat leathery. Color: Developing and fully expanded foliage, upper surface: 147A. Developing and fully expanded foliage, lower surface: 147B. Venation, upper and lower surfaces: 147B. Petiole: Length: About 7.5 cm. Diameter: About 2 mm. Texture, upper and lower surfaces: Pubescent. Color, upper and lower surfaces: 146B.

Flower description:

*Flower arrangement and type.*—Semi-double rounded flowers arranged in hemispherical umbels arising from apical leaf axils. Umbels displayed above the foliage. At full flowering, usually about 24 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 7 cm. Diameter: About 11 cm. Number of flowers and flower buds per umbel: Freely flowering, about 30. Flower diameter: About 4.3 cm. Flower depth (height): About 2.5 cm.

*Flower buds.*—Length: About 1.9 cm. Diameter: About 1 cm. Shape: Ovoid. Color: 45B.

*Petals.*—Quantity/arrangement: About five petals in a single whorl with typically three petaloids per flower; imbricate. Length: About 2.5 cm. Width: About 2.5 cm. Shape: Obovate. Apex: Rounded. Base: Acute. Margin: Entire. Texture, upper and lower surfaces: Smooth; satiny. Aspect: Slightly cupped. Color: When opening, upper surface: 46B. When opening, lower surface: 44A. Fully opened, upper surface: Brighter than 43A; at the base, 155D; venation, 45B. Fully opened, lower surface: 43B; at the base, 43D; venation, 45C.

*Petaloids.*—Length: About 2 cm. Width: About 1.3 cm. Shape: Obovate. Apex: Emarginate. Base: Acute. Margin: Entire. Texture, upper and lower surfaces: Smooth; satiny. Aspect: Slightly cupped. Color: When opening, upper surface: 46B. When opening, lower surface: 44A. Fully opened, upper surface: Brighter than 43A; at the base, 155D; venation, 45B. Fully opened, lower surface: 43B; at the base, 43D; venation, 45C.

*Sepals.*—Quantity/arrangement: Five per flower in a single whorl; not imbricate on open flowers. Length: About 1.5 cm. Width: About 3 mm. Shape: Lanceolate. Apex: Acuminate. Margin: Entire. Texture, upper and lower surfaces: Pubescent. Color, upper surface: 144A. Color, lower surface: Towards the apex, 144A; towards the base, 59A.

*Peduncle* (*umbel stem*).—Length: About 18.5 cm. Diameter: About 4 mm. Angle: About 30 to 45° from vertical. Strength: Strong. Texture: Pubescent. Color: 144A.

*Pedicel* (*individual flower stem*).—Length: About 3.8 cm. Diameter: About 1.5 mm. Angle: Erect to about 60° from vertical. Strength: Strong. Texture: Pubescent. Color: 183B.

*Reproductive organs.*—Androecium: Anther quantity: About eight per flower. Anther size: About 1 mm wide by 2 mm long. Anther shape: Oval. Anther color: 48B. Pollen amount: Scarce. Pollen color: 34A. Gynoecium: Pistil quantity: One per flower. Pistil length: About 8 mm. Stigma shape: Five-parted, star-shaped. Stigma color: 46A. Style length: About 2 mm. Style color: 46B. Ovary color: 138C.

*Seed/fruit.*—Seed and fruit development has not been observed.

Disease/pest resistance: Resistance to pathogens and pests common to *Pelargonium* has not been observed.

It is claimed:

1. A new and distinct cultivar of *Geranium* plant named 'Clips Redthree', as herein illustrated and described.

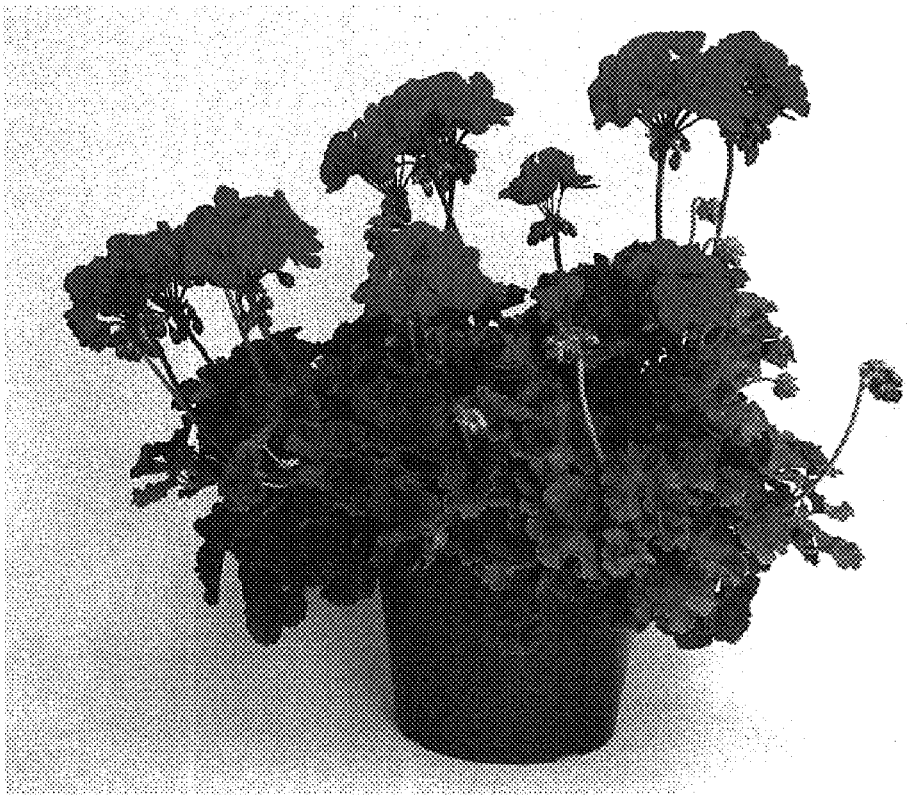
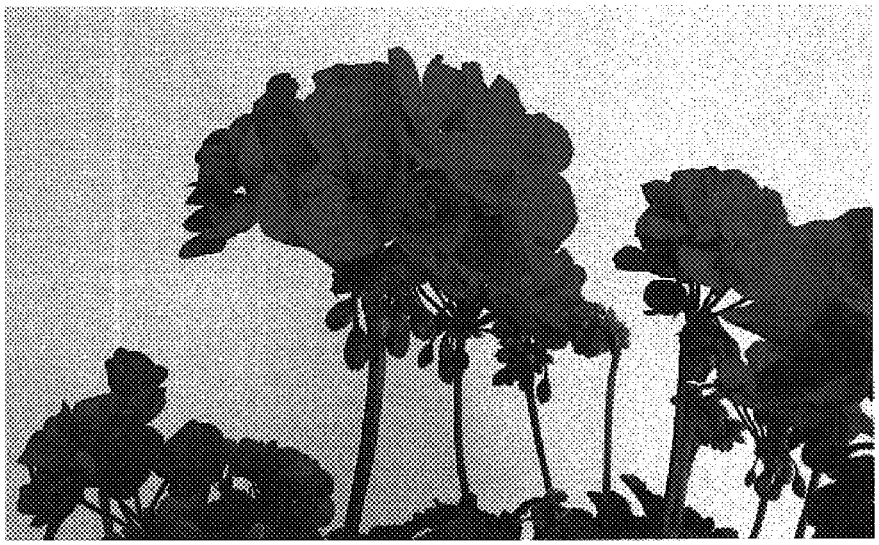

* * * * *